United States Patent
Al-Askar et al.

(10) Patent No.: US 10,555,690 B1
(45) Date of Patent: Feb. 11, 2020

(54) STANDING POSTURE MEASURING DEVICE

(71) Applicants: Fatma Al-Askar, Kuwait (KW); Dana Tawfiqi, Kuwait (KW); Murtada Khajah, Kuwait (KW); Saud Al-Obaidi, Kuwait (KW)

(72) Inventors: Fatma Al-Askar, Kuwait (KW); Dana Tawfiqi, Kuwait (KW); Murtada Khajah, Kuwait (KW); Saud Al-Obaidi, Kuwait (KW)

( * ) Notice: Subject to any disclaimer, the term of this patent is extended or adjusted under 35 U.S.C. 154(b) by 0 days.

(21) Appl. No.: 16/429,189

(22) Filed: Jun. 3, 2019

(51) Int. Cl.
*A61B 5/11* (2006.01)
*A61B 5/00* (2006.01)
*A61B 5/107* (2006.01)

(52) U.S. Cl.
CPC .......... *A61B 5/1116* (2013.01); *A61B 5/1072* (2013.01); *A61B 5/4561* (2013.01); *A61B 5/0064* (2013.01); *A61B 5/1071* (2013.01); *A61B 5/112* (2013.01); *A61B 5/1121* (2013.01); *A61B 5/4023* (2013.01); *A61B 5/743* (2013.01)

(58) Field of Classification Search
CPC ... A61B 5/1116; A61B 5/1121; A61B 5/1072; A61B 5/1077; A61B 5/4561; A61B 5/4566; A61B 5/4538; A61B 5/107
See application file for complete search history.

(56) References Cited

U.S. PATENT DOCUMENTS

| | | | |
|---|---|---|---|
| 6,962,568 B1 * | 11/2005 | Morger | A61B 5/1036 600/595 |
| 7,526,071 B2 * | 4/2009 | Drapeau | A61B 5/0064 378/163 |
| 9,149,222 B1 | 10/2015 | Zets et al. | |
| 2007/0171393 A1 * | 7/2007 | Cho | G01C 3/08 356/4.01 |
| 2009/0078471 A1 * | 3/2009 | Hulburt | G01G 19/44 177/126 |
| 2016/0278683 A1 | 9/2016 | Naito et al. | |

FOREIGN PATENT DOCUMENTS

| | | |
|---|---|---|
| CN | 105581882 A | 5/2016 |
| JP | 2014204759 A | 10/2014 |

OTHER PUBLICATIONS

S.A.M. Mark VIII "The Original Spinal Analysis Machine", ScripHessco—Chiropractic Equipment website, © 2018: https://www.scriphessco.com/products/sam-mark-viii/.

* cited by examiner

*Primary Examiner* — Patrick Fernandes
(74) *Attorney, Agent, or Firm* — Richard C. Litman; Nath, Goldberg & Meyer

(57) ABSTRACT

A standing posture measuring device provides a comprehensive objective analysis of the standing posture of a patient by measuring shoulder inclination, pelvic tilt in both frontal and sagittal planes, leg length discrepancy, and the difference in weight bearing of each leg. The device includes a base with two vertical side poles extending upward therefrom. The poles include electronic rulers for measuring leg lengths, while the base includes a weight scale for each foot for measuring a difference in weight bearing. The poles also support a shoulder inclination instrument and a pelvic inclination instrument that measures both lateral pelvic tilt and the angle of pelvis tilt in the sagittal plane.

7 Claims, 4 Drawing Sheets

STANDING POSTURE MEASURING DEVICE

BACKGROUND

1. Field

The disclosure of the present patent application relates to physical therapy devices, and particularly to a standing posture measuring device.

2. Description of the Related Art

Physical therapists frequently need to measure the orientation or tilt of one or more parts of the body while a patient is standing, in order to provide a comprehensive assessment of the patient's posture.

Although of significant importance, shoulder inclination has no currently known clinical method of measurement. A difference in height between shoulders may be an indication of muscle spasms or weaknesses in the muscles surrounding the shoulder and neck. As such, a reliable measurement of shoulder inclination can be very beneficial for both patient and physical therapist.

Lateral pelvic tilt (LPT) is the deviation of the pelvis in the frontal plane, which is measured by the difference in height between the left and right iliac crests. The iliac crests are located on the superior and lateral edge of the ilium very close to the surface of the skin in the hip region. The pelvis will "hip hike" to the side of relative weak glute medius, tight quadratus lumborum and tight adductors and will "hip drop" to the side of relative tight glute medius, weak quadratus lumborum and weak/elongated adductors. Lateral pelvic tilt deviations are accompanied with muscular imbalance which could in turn lead to low back pain and postural abnormalities along with increasing chances of the patient acquiring a herniated disc, a degenerating disc, and/or sacroiliac joint pain.

The angle of pelvis tilt describes the orientation of the pelvis in the sagittal plane. It is measured by the angle formed between a line passing the anterior superior iliac spine (ASIS) and the posterior superior iliac spine (PSIS) and the horizontal. The orientation of the pelvis is determined by the muscular and ligamentous forces that act upon it. When the pelvis is in a position of forward rotation, known as anterior pelvic tilt (APT) it is associated with an increase in the lordotic curvature of the lumbar spine along with weakness in both hip extensors and abdominals, and tightness of hip flexors. Alternately, backward rotation of the pelvis, known as posterior pelvic tilt (PPT), is usually accompanied by decreased lordosis of the lumbar spine, weak hip flexors along with both tight hamstrings and hip extensors. Any deviation from the normal alignment of the pelvis will affect the kinetic chain of the body leading to forward head position, shoulder malalignment, distorted gait and abnormal postures curvatures at the thoracic, cervical and lumbar spines.

Available methods for sagittal plane analysis of the pelvic tilt include the trigonometric method and the radiographic method. One limitation of the trigonometric method is that it can take up to 20 minutes to obtain the angle for both sides of the pelvic. Additionally, the trigonometric method also requires multiple pieces of equipment. Currently, the device most commonly used in the clinical setting is caliper-based inclinometers like the palpation meter (PALM). As the PALM must be mounted around the therapist's neck, however, the resulting measurement may be affected by the changing posture of the therapist. While the radiographic method is used for measuring pelvic tilt, it is clinically expensive and invasive involving potentially harmful radiation.

Due to the importance of assessing pelvic angles for good posture alignment in standing and its influence on other body segments, there is a need for an objective tool or measurement of the static posture in both the frontal and sagittal planes and for the relevant body parts in static position.

Leg length discrepancy is the difference in length between each leg. This measurement is of special importance because it alerts the therapist to bigger malalignments in the body that may extend to scoliosis. If detected early in the clinical setting, proper management can be performed and further malalignments can be reduced or avoided altogether. Currently in the clinic, this is done by using a normal tape measure to measure between known bony marks in the leg and comparing measurements obtained for each leg.

A difference in a patient's weight bearing can be detected by measuring the weight bearing on each leg/foot. A difference in the patient's weight may be an indication of postural malalignment and kinetic chain abnormalities. It is important for a patient to knowing of any differences in weight bearing so that the patient can take steps to correct it.

Several prior art devices are currently used by physical therapists. Ultrasonic measuring devices can be used to determine a relative spatial position of points of interest located in ultrasound images. Some body measuring apparatus require extensive training prior to use and/or patient preparation. Some devices include a wearable tool surrounding the upper body of a user. These wearable units are not suitable for all body types and involve a level of discomfort for the patient.

There is no known device that has the ability to provide a minimally invasive, global static postural analysis in one static standing position by measuring shoulder inclination, pelvic tilt in both frontal and sagittal planes, leg length discrepancy and the difference in weight bearing on each leg.

Thus a standing posture measuring device solving the aforementioned problems is desired.

SUMMARY

The standing posture measuring device can measure shoulder inclination; pelvic tilt in both frontal and sagittal planes; leg length discrepancy; and the difference in weight bearing on each leg. The standing posture measuring device, also referred to herein, as a three dimensional postural technical analysis ("3DPTA") device, includes a base with two vertical side poles extending upward therefrom. The base includes a weight scale for each foot for measuring a difference in weight bearing. An upper rear bar and lower rear bar extend between the poles.

The upper rear bar is a horizontal arm that can be adjusted to be at shoulder level of different height patients and supports a shoulder inclination instrument. The shoulder inclination instrument includes two pointers mounted at locations that correspond to the patient's acromion processes and an upper centrally located electronic spirit level that displays the degree of angle between the two acromion pointers, which is the angle of shoulder inclination.

The lower rear bar is a horizontal arm that can be adjusted to be at hip level of different height patients and supports a pelvic inclination instrument. The pelvic inclination instrument is capable of measuring both lateral pelvic tilt (LPT) and the angle of pelvis tilt in the sagittal plane. It includes right and left movable arms and a lower centrally located electronic spirit level that displays the degree of pelvic tilt.

The standing posture measuring device provides an easier, faster way of measuring leg lengths using laser rulers that are slidingly mounted on the vertical side poles. Each laser ruler includes a laser housing with a downwardly directed laser, a laser support band for mounting the housing to the side pole and a laser display for displaying the length of the corresponding leg in centimeters.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
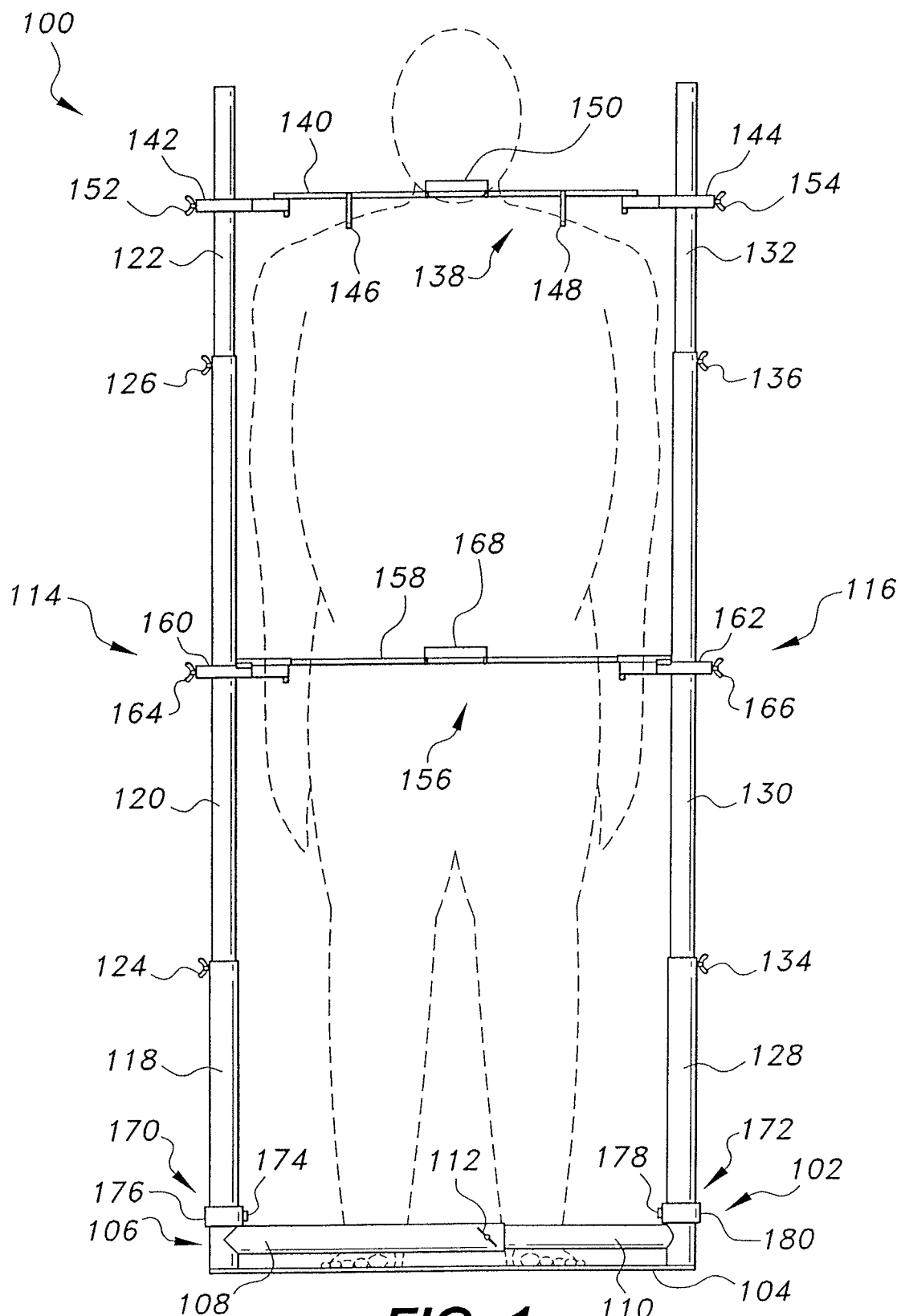
FIG. 1 is an environmental, front view of a standing posture measuring device.
Figure 2:
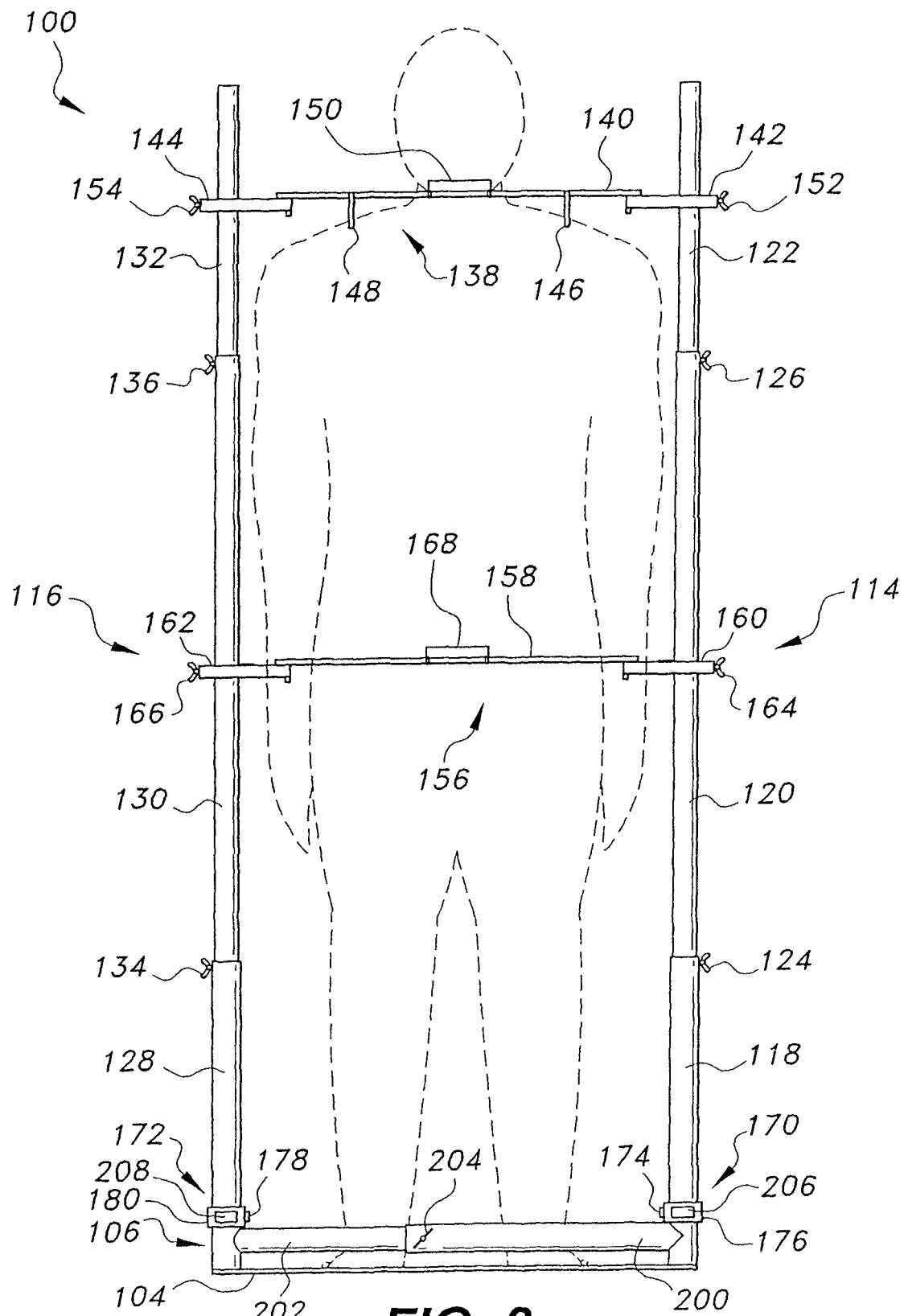
FIG. 2 is an environmental, rear view of the standing posture measuring device of FIG. 1.
Figure 3:
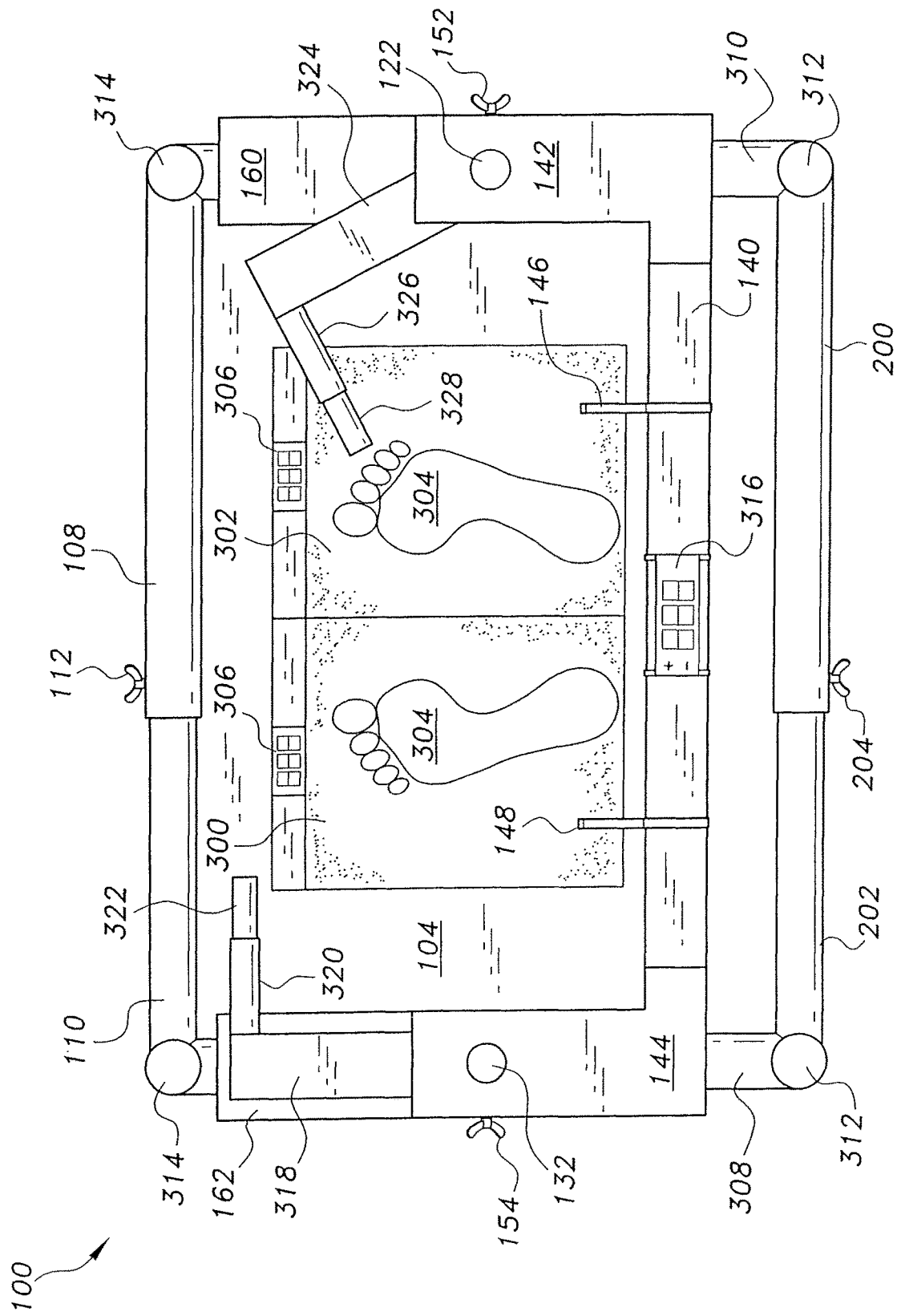
FIG. 3 is a plan view of the standing posture measuring device of FIG. 1.
Figure 4:
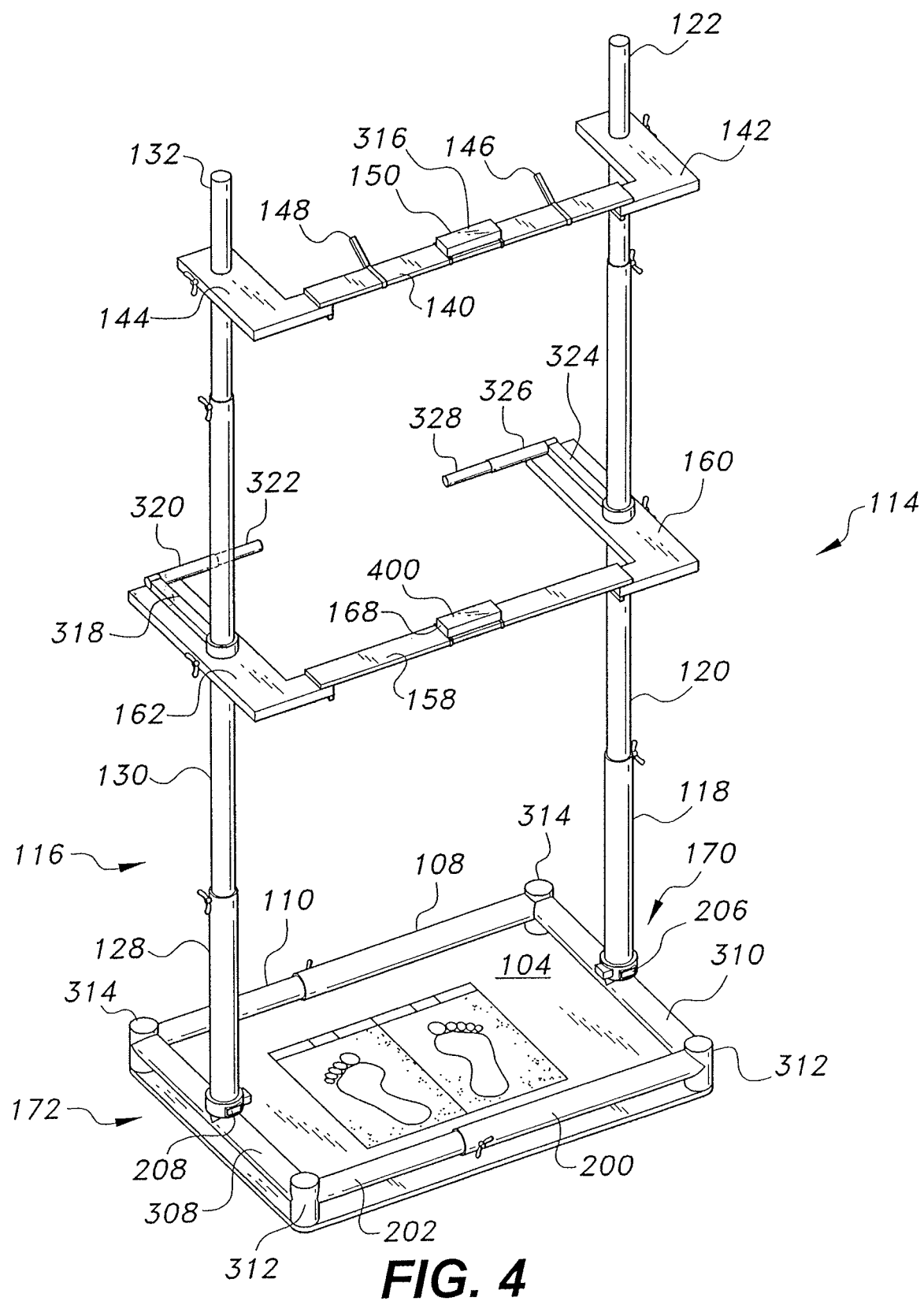
FIG. 4 is a perspective view of the standing posture measuring device of FIG. 1.

A standing posture measuring device 100 is shown in FIGS. 1-4. The standing posture measuring device 100 includes a base 102, with a base platform 104 and a rectangular base frame 106. As best seen in FIGS. 3 and 4, the base platform 104 provides a horizontal support for a weight distribution measuring system that includes a left electronic weight scale 300, a right electronic weight scale 302, and a foot outline indicia 304 for indicating where, approximately, a patient should stand. Each electronic weight scale includes a digital display 306 for indicating the amount of weight bearing of each foot.

The base frame 106 includes: a right front tube 108; a left front tube 110; a right rear tube 200; a left rear tube 202; a left side tube 308 and a right side tube 310. As best seen in FIG. 3, the rear tubes 200, 202 are connected to the side tubes 310, 308 respectively, at rear corner posts 312, while the front tubes 108, 110 are connected to the side tubes 310, 308 respectively, at front corner posts 314. The connections between the tubes are approximately (within manufacturing tolerances) at right angles, thereby forming the rectangular base frame 106. The left front tube 110 is telescopically mounted within the right front tube 108, while the left rear tube 202 is telescopically mounted within the right rear tube 200, to thereby allow adjustment of the width of the rectangular base frame 106. A front tube locking wing-screw 112 extends through a threaded hole in the right front tube 108 and contacts the outer surface of the left front tube 110, to thereby lock the tubes 108, 110 in position relative to one another. Similarly, a rear tube locking wing-screw 204 extends through a threaded hole in right rear tube 200 and contacts the outer surface of the left rear tube 202, to thereby lock the tubes 200, 202 in position relative to one another. The wing-screws 112, 204 include wings to facilitate manual adjustment of the width of the standing posture measuring device 100, without the need for tools.

The standing posture measuring device 100 further includes a right instrument support frame 114 and a left instrument support frame 116. The right instrument support frame 114 includes: a right base pole 118 removably and vertically connected to the center of the right side tube 310 (FIG. 4); a lower right adjustable pole 120 telescopically mounted within the right base pole 118; and an upper right adjustable pole 122 telescopically mounted within the lower right adjustable pole 120. The right instrument support frame 114 further includes a lower right pole locking wing-screw 124 and an upper right pole locking wing-screw 126, to thereby lock the lower right adjustable pole 120 to the right base pole 118 and the upper right adjustable pole 122 to the lower right adjustable pole 120, respectively. Similarly, the left instrument support frame 116 includes: a left base pole 128 removably and vertically connected to the center of the left side tube 308 (FIG. 4); a lower left adjustable pole 130 telescopically mounted within the left base pole 128; and an upper left adjustable pole 132 telescopically mounted within the lower left adjustable pole 130. The left instrument support frame 116 further includes a lower left pole locking wing-screw 134 and an upper left pole locking wing-screw 136, to thereby lock the lower left adjustable pole 130 to the left base pole 128 and the upper left adjustable pole 132 to the lower left adjustable pole 130, respectively. The instrument support frames support further instruments as described below and are adjustable in height to accommodate different heights and proportions of patients.

The standing posture measuring device 100 further includes a shoulder inclination instrument 138 including an upper rear bar 140 that can be adjusted to be at a shoulder level of a patient. The upper rear bar 140 is slidingly supported on an upper right support bracket 142 and an upper left support bracket 144. The upper right support bracket 142 includes a hole through which the upper right adjustable pole 122 extends. An upper right bracket locking wing-screw 152, extends through a threaded hole in the upper right support bracket 142 and contacts the upper right adjustable pole 122, to thereby lock the upper right support bracket 142 thereto. Similarly, the upper left support bracket 144 includes a hole through which the upper left adjustable pole 132 extends. An upper left bracket locking wing-screw 154, extends through a threaded hole in the upper left support bracket 144 and contacts the upper left adjustable pole 132, to thereby lock the upper left support bracket 144 thereto. Two acromion pointers 146, 148 are mounted on the upper rear bar 140 at locations that correspond to the patient's right and left acromion processes, respectively. In human anatomy, the acromion is a bony process on the scapula (shoulder blade) that extends laterally over the shoulder joint. An upper centrally located electronic spirit level 150 is mounted on the top surface of the upper rear bar 140 and includes a digital display 316 for indicating the shoulder inclination as described below.

To measure shoulder inclination, a technician first directs a patient to stand fully erect and forwardly on the base platform 104 such that the patient's left foot is on the left electronic weight scale 300 and the patient's right foot is on the right electronic weight scale 302, using the foot outline indicia 304 as a guide. A digital scale display 306 indicates the weight exerted by each foot. Preferably, the patient's stance results in equal weight applied by both feet. The technician then adjusts the upper right support bracket 142 up or down on the upper right adjustable pole 122 and the upper left support bracket 144 up or down on the upper left adjustable pole 132, until the right acromion pointer 146 contacts the patient's right acromion process and the left acromion pointer 148 contacts the patient's left acromion process. The technician then uses the upper right bracket locking wing-screw 152, and the upper left bracket locking wing-screw 154 to lock the brackets 142, 144 and the upper bar 140 in position. A difference in the alignment of the brackets 142, 144 can be detected by the electronic spirit level 150 to indicate a height difference between shoulders. The height difference can be determined from the digital display 316 of the electronic spirit level 150.

The standing posture measuring device 100 further includes a pelvic inclination instrument 156 that is mounted on a lower rear bar 158 that can be adjusted to be at a hip level of a patient. The pelvic inclination instrument 156 is capable of assessing both lateral and saggital pelvic tilt (LPT). The lower rear bar 158 is slidingly supported on a lower right support bracket 160 and a lower left support bracket 162. The lower right support bracket 160 includes a hole through which the lower right adjustable pole 120 extends. A lower right bracket locking wing-screw 164, extends through a threaded hole in the lower right support bracket 160 and contacts the lower right adjustable pole 120, to thereby lock the lower right support bracket 160 thereto. Similarly, the lower left support bracket 162 includes a hole through which the lower left adjustable pole 130 extends. A lower left bracket locking wing-screw 166, extends through a threaded hole in the lower left support bracket 162 and contacts the lower left adjustable pole 130, to thereby lock the lower left support bracket 162 thereto. The lower right support bracket 160 includes a right movable arm holder 324 and first 326 and second 328 right movable arms. The first right movable arm 326 is slidingly mounted to the right movable arm holder 324, while the second right movable arm 328 is telescopically mounted in the first right movable arm 326. The lower left support bracket 162 includes a left movable arm holder 318 and first 320 and second 322 left movable arms. The first left movable arm 320 is slidingly mounted to the left movable arm holder 318, while the second left movable arm 322 is telescopically mounted in the first left movable arm 320. The movable arm holders 318, 324 are rotatably mounted on the upper adjustable poles 132, 122, respectively, to allow angular adjustment of the moveable arms 320, 322, 326, 328, in addition to the length adjustment provided by the telescopic and sliding connections described above. A lower centrally located electronic spirit level 168 is mounted on the top surface of the lower rear bar 158 and includes a digital display 400 for indicating the pelvic tilt as described below.

To measure the patient's lateral pelvic tilt (LPT) or deviation of the pelvis in the frontal plane, the pelvic inclination instrument 156 measures the difference in height between the left and right iliac crests. As done when measuring the patient's shoulder inclination, the technician first directs the patient to stand fully erect and forwardly on the base platform 104 such that the patient's left foot is on the left electronic weight scale 300 and the patient's right foot is on the right electronic weight scale 302, using the foot outline indicia 304 as a guide. A digital scale display 306 indicates the weight exerted by each foot. Preferably, the patient's stance results in equal weight applied by both feet. The technician then adjusts the lower left support bracket 162 up or down on the lower left adjustable pole 130 and adjusts the left movable arm holder 318 and the left movable arms 320, 322 until the end of the second left movable arm 322 contacts the patient's left iliac crest. The technician then uses the lower left bracket locking wing-screw 166 to lock the bracket 162 and the left end of the lower bar 158 in position. The technician then adjusts the lower right support bracket 160 up or down on the lower right adjustable pole 120 and adjusts the right movable arm holder 324 and the right movable arms 326, 328 until the end of the second right movable arm 328 just contacts the patient's right iliac crest. The technician then uses the lower right bracket locking wing-screw 164 to lock the bracket 160 and the right end of the lower bar 158 in position. The patient's LPT (difference in height between the left and right iliac crests) can then be read on the digital display 400 of the lower centrally located electronic spirit level 168.

To measure the patient's sagittal pelvic tilt, which is the deviation of the anterior superior iliac spine (ASIS) and the posterior superior iliac spine (PSIS) of the pelvis, the pelvic inclination instrument 156 measures the difference in height between the left (or right) ASIS and the right (or left) PSIS. As done with the previously described procedures, the technician first directs the patient to stand fully erect and forwardly on the base platform 104 such that the left foot is on the left electronic weight scale 300 and the right foot is on the right electronic weight scale 302, using the foot outline indicia 304 as a guide. A digital scale display 306 indicates the weight exerted by each foot. Preferably, the patient's stance results in equal weight applied by both feet. The technician then adjusts the lower left support bracket 162 up or down on the lower left adjustable pole 130 and adjusts the left movable arm holder 318 and the left movable arms 320, 322 until the end of the second left movable arm 322 just contacts the patient's left ASIS (or PSIS). The technician then uses the lower left bracket locking wing-screw 166 to lock the bracket 162 and the left end of the lower bar 158 in position. The technician then adjusts the lower right support bracket 160 up or down on the lower right adjustable pole 120 and adjusts the right movable arm holder 324 and the right movable arms 326, 328 until the end of the second right movable arm 328 just contacts the patient's right PSIS (or ASIS). The technician then uses the lower right bracket locking wing-screw 164 to lock the bracket 160 and the right end of the lower bar 158 in position. The patient's sagittal pelvic tilt can then be read on the digital display 400 of the lower centrally located electronic spirit level 168. It should be noted that it may be useful to take the measurements in both directions (left ASIS to right PSIS and right PSIS to left ASIS) and the patient's LPT may need to be taken into account when determining the patient's actual sagittal pelvic tilt.

The standing posture measuring device 100 further includes a leg measuring instrument that includes a right laser ruler 170 for measuring the patient's right leg length and a left laser ruler 172 for measuring the patient's left leg length. The right laser ruler 170 includes a right laser housing 174, a right laser support band 176 and a right laser display 206. The right laser support band 176 mounts the right laser ruler 170 on right base pole 118 and may include a slot or other structure to allow the right laser ruler 170 to slide above the lower right pole locking wing-screw 124, if required. Similarly, the left laser ruler 172 includes a left laser housing 178, a left laser support band 180 and a left laser display 208. The left laser support band 180 mounts the left laser ruler 172 on left base pole 128 and may include a slot or other structure to allow the left laser ruler 172 to slide above the lower left pole locking wing-screw 134, if required.

To measure the patient's leg length, as done with the previously described procedures, the technician first directs the patent to stand fully erect and forwardly on the base platform 104 such that the left foot is on the left electronic weight scale 300 and the right foot is on the right electronic weight scale 302, using the foot outline indicia 304 as a guide. A digital scale display 306 indicates the weight exerted by each foot. Preferably, the patient's stance results in equal weight applied by both feet. The technician then raises the left or right laser ruler 170, 172 to the level of the iliac crest. A downwardly directed laser beam is directed from the associated laser housing 174, 178 to the platform 104 to measure leg height. The time the laser takes to travel to and from the platform 104 is converted to distance, as is known in laser-based "tape" measures. The length of each leg is displayed on the corresponding display 206, 208 in centimeters (or other desired units).

It is to be understood that the standing posture measuring device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A standing posture measuring device, consisting of:
    a base including a base platform and a base frame;
    a right instrument support frame mounted on the base frame;
    a left instrument support frame mounted on the base frame;
    a shoulder inclination instrument including an upper rear bar supported on the right and left instrument support frames, the upper rear bar having a top surface, the shoulder inclination instrument comprising:
        a right acromion pointer mounted on the upper rear bar at a first location that corresponds to a patient's right acromion process;
        a left acromion pointer mounted on the upper rear bar at a second location that corresponds to a patient's left acromion process; and
        an upper electronic spirit level mounted on the top surface of the upper rear bar and having an upper digital display for indicating shoulder inclination;
    a pelvic inclination instrument comprising:
        a lower rear bar supported on the right and left instrument support frames;
        a first right movable arm;
        a first left movable arm; and
        a lower electronic spirit level mounted on the top surface of the lower rear bar and having a lower digital display for indicating pelvic inclination;
    a leg measuring instrument, wherein the leg measuring instrument comprises:
        a right laser ruler having a right laser housing, a right laser support band supported on the right instrument support frame and a right laser display; and
        a left laser ruler having a left laser housing, a left laser support band supported on the left instrument support frame and a left laser display.

2. The standing posture measuring device according to claim 1 wherein the base platform comprises a weight distribution measuring system comprising:
    a left electronic weight scale with a first digital display for indicating the weight resting on the left electronic weight scale; and
    a right electronic weight scale with a second digital display for indicating the weight resting on the right electronic weight scale.

3. The standing posture measuring device according to claim 2, wherein the base platform includes foot outline indicia for indicating where feet should be placed on the left and right electronic weight scales.

4. The standing posture measuring device according to claim 1, wherein the base frames has a width and a depth and comprises:
    a right front tube;
    a left front tube;
    a right rear tube;
    a left rear tube;
    a left side tube; and
    a right side tube; wherein
    the front tubes are connected to the sides tubes at right angles and the rear tubes are connected to the sides tubes at right angles, such that the base frame is generally rectangular.

5. The standing posture measuring device according to claim 4, wherein:
    the left front tube is telescopically mounted within the right front tube; and
    the left rear tube is telescopically mounted within the right rear tube, to thereby allow adjustment of the width of the base frame.

6. The standing posture measuring device according to claim 4, wherein:
    the right instrument support frame comprises:
        a right base pole vertically connected to a center of the right side tube;
        a lower right adjustable pole telescopically mounted within the right base pole; and an upper right adjustable pole telescopically mounted within the lower right adjustable pole; and wherein
    the left instrument support frame comprises:
        a left base pole vertically connected to a center of the left side tube;
        a lower left adjustable pole telescopically mounted within the left base pole; and an upper left adjustable pole telescopically mounted within the lower left adjustable pole.

7. The standing posture measuring device according to claim 6, wherein
    the right instrument support frame comprises an upper right support bracket and a lower right support bracket;
    the left instrument support frame comprises an upper left support bracket and a lower left support bracket;
    the upper rear bar is slidingly supported on the upper right support bracket and the upper left support bracket;
        the upper right support bracket comprises a hole through which the upper right adjustable pole extends; and
        the upper left support bracket includes a hole through which the upper left adjustable pole extends; and
    the lower rear bar is slidingly supported on the lower right support bracket and the lower left support bracket;
    the lower right support bracket comprises:
        a hole through which the lower right adjustable pole extends; and
        a right movable arm holder that supports the first right movable arm; and
    the lower left support bracket comprises:
        a hole through which the lower left adjustable pole extends; and
        a left movable arm holder that supports the first left movable arm.

* * * * *